(12) United States Patent
Harris et al.

(10) Patent No.: US 8,961,958 B2
(45) Date of Patent: Feb. 24, 2015

(54) HIGH CONCENTRATION SELF-MICROEMULSIFYING COENZYME Q10 PREPARATIONS FOR NUTRITIONAL USE

(75) Inventors: Steven B. Harris, Ontano, CA (US); Nick J. Huang, San Bernadino, CA (US)

(73) Assignee: Bioavailability, Inc, Rancho Cucamonga, CA (US)

( * ) Notice: Subject to any disclaimer, the term of this patent is extended or adjusted under 35 U.S.C. 154(b) by 1504 days.

(21) Appl. No.: 11/667,800

(22) PCT Filed: Nov. 16, 2004

(86) PCT No.: PCT/US2004/038273
§ 371 (c)(1),
(2), (4) Date: May 14, 2007

(87) PCT Pub. No.: WO2006/080903
PCT Pub. Date: Aug. 3, 2006

(65) Prior Publication Data
US 2009/0060891 A1    Mar. 5, 2009

(51) Int. Cl.
| | | |
|---|---|---|
| *A61K 8/30* | (2006.01) |
| *A61K 38/43* | (2006.01) |
| *A61K 38/54* | (2006.01) |
| *A61K 9/48* | (2006.01) |
| *A23L 1/00* | (2006.01) |
| *A23L 1/035* | (2006.01) |
| *A23L 1/30* | (2006.01) |
| *A61K 9/107* | (2006.01) |

(52) U.S. Cl.
CPC ............ *A61K 9/4858* (2013.01); *A23L 1/0029* (2013.01); *A23L 1/035* (2013.01); *A23L 1/30* (2013.01); *A61K 9/1075* (2013.01)
USPC ........................ 424/94.1; 424/70.31; 424/94.3

(58) Field of Classification Search
CPC . A61K 2300/00; A61K 36/82; A61K 31/355; A61K 2800/412; A61K 2800/592; A61K 2800/652; A61K 31/00; A61K 31/05; A61K 31/202; A61K 31/203; A61K 31/353; A61K 31/66; A61K 31/7048; A61K 36/16; A61K 36/185; A61K 36/258
See application file for complete search history.

(56) References Cited

U.S. PATENT DOCUMENTS

| | | | |
|---|---|---|---|
| 4,824,669 A | 4/1989 | Folkers et al. |
| 5,035,895 A | 7/1991 | Shibusawa et al. |
| 6,056,971 A | 5/2000 | Goldman |
| 6,740,338 B1 | 5/2004 | Chopra |
| 2003/0165438 A1 | 9/2003 | Behnam |
| 2004/0152612 A1 | 8/2004 | Supersaxo et al. |
| 2005/0147598 A1 | 7/2005 | Ueda et al. |

FOREIGN PATENT DOCUMENTS

| | | |
|---|---|---|
| EP | 0 617 957 A1 | 10/1994 |
| EP | 1 475 363 A1 | 11/2004 |
| GB | 2184355 A | 6/1987 |
| JP | 58-013508 | 1/1983 |
| JP | 58-077810 | 5/1983 |
| JP | 2000-212066 | 8/2000 |
| JP | 2003-026625 | 1/2003 |
| JP | 2003-238396 | 8/2003 |
| JP | 2003/300870 | 10/2003 |
| JP | 3549522 B1 | 4/2004 |
| JP | 2004-210669 | 7/2004 |
| WO | WO 9957995 | 11/1999 |
| WO | WO 03/007907 | 1/2003 |
| WO | WO 03/041632 A2 | 5/2003 |

*Primary Examiner* — Debbie K Ware
(74) *Attorney, Agent, or Firm* — Jay P. Hendrickson

(57) ABSTRACT

A method and composition are presented for enhancing the dissolution and bioavailable properties of CoQ10 nutritional supplements and/or therapeutic agents for a human being and other mammals. The method includes preparing an anhydrous self-microemulsifying base composition by combining: CoQ10, a water-immiscible, and a non-ionic surfactant, containing polyethylene glycol. For an orally administered CoQ10 nutritional supplement in a capsule formulation, a unit dosage from the composition is added to a dissolvable capsule, preferably a soft gelatin capsule, in order to form the nutritional supplement. When a capsule containing the self-microemulsifying composition enters the digestive tract, the temperature of the body's digestive juices warms the composition, causing any of the CoQ10 that may have re-crystallized out of the composition to become re-dissolved into the composition before the capsule dissolves. The re-dissolution of CoQ10 is bioavailable when the capsule dissolves. Upon dissolution of the capsule, the self-microemulsifying composition comes into contact with the digestive juices and naturally forms micellar-type bioavaible microemulsions, consisting of micelles containing CoQ10. In addition to the capsule formulation, the invention includes parenteral, liquid, topical and ophthalmic formulations.

45 Claims, No Drawings

HIGH CONCENTRATION SELF-MICROEMULSIFYING COENZYME Q10 PREPARATIONS FOR NUTRITIONAL USE

RELATED APPLICATION

This application relates to and claims the priority and benefits under 35 U.S.C. 371 of international patent application PCT/US2004/038273 filed on Nov. 16, 2004.

FIELD OF THE INVENTION

The present invention relates to a method and composition for providing high concentrations of coenzyme Q10 in a self-microemulsifyable base composition for use as a nutritional supplement and/or therapeutic agent.

BACKGROUND OF THE INVENTION

Generally, coenzyme Q (hereafter referred to as "CoQ") is a class of isoprenoid quinone or quinol physiological substances occurring as component factors in connection with the mitochondrial electron transfer system within a living cell. More specifically, CoQ acts as an electron carrier in oxidative phosphorylation reactions, through metabolic pathways, particularly aerobic pathways, to produce ATP and, as a result, energy. CoQ occurs in specific forms generally designated CoQsubn or CoQn, where n stands for the number of isoprenoid units attached as a side chain to the quinone/quinol portion of the molecule. Different species employ different n length CoQ molecules for electron transfer. For example, CoQ9 has 9 isoprenoid units in the side chain, and is the most common form of CoQ in rodents. CoQ10 has 10 units and is the most common form of CoQ in humans, although shorter forms are found in humans, and may serve as precursors for CoQ10.

Further, any of the CoQ molecules in living organisms may occur in the oxidized (quinone) or reduced (quinol) form naturally, and indeed one form is converted to the other in the normal electron transfer process.

The use of CoQ10, also known as ubidecarenone in oxidized form or ubiquinol in reduced form, as a human nutritional supplement is well established. CoQ10 is involved in important physiological functions in humans such as: stimulating the immune system, enhancing circulation, strengthening the cardiovascular system and in general contributing to the cellular mitochondrial generation of energy. CoQ10 deficiencies have been associated with several serious human diseases such as: diabetes, asthma, cancer, Alzheimer's disease, multiple sclerosis, muscular dystrophy, degenerative heart conditions, and mental deficiencies. Additionally, there is some indication that the demand for CoQ10 increases in healthy persons who are physically fatigued and in persons with cardiovascular disease and other chronic diseases, and in persons receiving prolonged pharmacotherapy. Accordingly, it may be therapeutically appropriate to administer CoQ10 supplements to patients suffering from such conditions.

One of the difficulties that is encountered in attempting to formulate CoQ10 supplements for human ingestion is that CoQ10 is nearly insoluble in water. Due to the fact that the digestive tract is a substantially aqueous system, it is difficult to provide CoQ10 in a form that is bioavailable, meaning that CoQ10 will be dispersed readily within the digestive tract in a form that will dissolve in the digestive juices and be absorbed by the body.

There have been numerous attempts to provide a CoQ10 supplement that is bioavailable. In this regard, one of the most recent attempts to formulate CoQ10 with enhanced bioavailable characteristics is disclosed in U.S. Pat. No. 6,056,971. The patent's preferred embodiment discloses the utilization of a mixture of surface active agents ("surfactants") as solubilizers, comprising SPAN type material (i.e., sorbitan fatty acid esters), which is generally oil soluble and dispersible but not completely soluble in water, and a TWEEN type material (polyethoxylated sorbitan fatty acid esters), which is generally soluble and dispersible in water. The patent states that the combination of the Span type material and Tween type material allows an adjustment of the ratio of the relative quantities of the two materials, which provides for obtaining an appropriate degree of water solubility or insolubility of the solubilized composition, i.e. hydrophilic versus lipophilic properties. The patent further discloses the utilization of a polyhydric alcohol which "serves the important function of avoiding the necessity of slowly adding water to form an aqueous phase [as disclosed in the prior art]". The liquid composition is prepared by mixing the solubilizers and polyhydric alcohol together, heating the mixture to a temperature of between "50° C. to 60° C.," adding the CoQ10 to the heated mixture, and finally adding a portion of the mixture, after it has cooled, to a soft gelatin capsule. The examples in the patent disclose that the procedure is capable of producing non-aqueous concentrations of CoQ10 of 3.55% of the weight of the composition.

Although U.S. Pat. No. 6,056,971 may provide a useful liquid composition for the delivery of CoQ10 in a non-aqueous form, the composition has several undesirable limitations. The most significant limitation is that a CoQ10 concentration of 3.55% by weight of the total composition is only marginally higher than a concentration of about 3%, which is attainable using oil-based compositions. Another limitation of the method disclosed in the patent is the use of polyhydric alcohols in the mixture, which is made necessary, in part, by the use of TWEEN-80 (polysorbate 80), which is a relatively solid and refractory surfactant when used with CoQ10 at room temperature, unless thinned by addition of a low molecular weight alcohol. Another limitation of the method disclosed in the patent is that the mixture of the solubilizers and polyhydric alcohol must be heated to relatively high temperatures of at least up to the melting point of pure CoQ10 crystals (about 48° C. to 52° C.) and then, after adding the CoQ10, the composition must be cooled in order to add it to a soft gelatin capsule. The inventors of the present invention have determined that as the liquid composition cools, significant quantities of CoQ10 crystals precipitate out of the solution. Because the precipitated CoQ10 crystals are no longer dissolved in the solubilized composition, many of the crystals formed in the capsule cannot be expected to be absorbed in the gastrointestinal tract when the capsule is ingested. As a result, the effective concentration of CoQ10 is actually substantially lower than the original concentration, because the crystals that have precipitated out of the composition will have much lower bioavailability, similar to that of crystalline dry oral CoQ10 preparations.

In addition to CoQ10 supplements that are administered orally, others have attempted to prepare CoQ10 supplements that are administered parenterally. U.S. Pat. No. 4,824,669 directs preparation of a clinically acceptable fatty emulsion which begins with CoQ10 dissolved in an oil phase; the oil phase is then mixed with aqueous media and homogenized by means of sonication or repeated passage of the mixture through a small orifice. This method uses no surfactant and is limited by difficult and tedious preparation steps. It is also limited by relatively low CoQ10 concentrations, which are reported at 7.5 to 30 microgram/mL, equivalent to 0.00075% to 0.003% by weight of the composition. This is only 10 to 40 times more concentrated than the normal human plasma concentration of CoQ10, which is about 0.75 microgram/mL.

U.S. Pat. No. 5,035,895 discloses the use of a complex mixture of 3 mg meglumin, 27 mg glycerin, 50 mg 70% solution of D-sorbitol, 10 mg CoQ10, and 10 mg egg yolk lecithin. The mixture is treated with a stirring machine and pure water is added to make up 1.0 ml. This patent discloses that the procedure is capable of achieving a CoQ10 concentration of 1%, but uses a difficult production method and ionic surfactants. Also, the use of egg yolk lecithin as an emulsifier requires that strict sterilization and single-patient-use procedures be followed in order to avoid microorganism growth in the emulsion media.

Accordingly, what is needed for the oral administration of a CoQ10 supplement is a self-microemulsifyable base composition, containing high concentrations of CoQ10 that will not re-crystallize and precipitate out of the base and, as a result, reduce the bioavailability of the CoQ10. Alternately, if some of the CoQ10 crystals do precipitate out of the composition at room temperature or lower, a base composition is needed that has the ability to re-dissolve the CoQ10 crystals into the base at body temperature (about 37° C.), before the soft gelatin capsule dissolves in the gastrointestinal tract and the composition comes into contact with gastric juices. Further, a base is needed that contains no alcohols but still forms a self-microemulsifying system with very small (12 nm to 25 nm) micelles, which is optimal for maximal CoQ10 dispersion. Most usefully, the composition should be simple, containing only 2 or 3 ingredients, and be easily made.

Further, what is needed is a parenterally administered CoQ10 supplement consisting of a self-microemulsifyable base composition, containing high concentrations of CoQ10 that will not re-crystallize and precipitate out of the base at room temperature and, as a result, make the product unsuitable for parenteral uses. Such a base could be injected directly in certain intramuscular uses, or it could be packaged as a sterile anhydrous liquid for use in preparing high concentration water-based microemulsions suitable for intravenous injection. These microemulsions could be prepared in a sterile vial by addition of physiologic water-based fluid followed by gentle shaking and mixing, in the same manner as lypholyzed products intended for intravenous injections (for example, antibiotics). The base should not contain emulsifiers which contain phosphorous or nitrogen (such as lecithin) which support the growth of microorganisms. In regard to sterilization, it would also be useful if the base composition and the microemulsions made from it were easily sterilized by ultra-filtration in order to minimize the risk of contamination.

The present invention overcomes the limitations described above and provides an efficient method for preparing a CoQ10 base composition for use in oral, topical and parenteral formulations, containing concentrations of CoQ10 that are substantially higher than has been previously achieved.

SUMMARY OF THE INVENTION

The present invention generally provides a method and a composition for enhancing the dissolution and bioavailable properties of CoQ10 nutritional supplements and/or therapeutic agents for a human being and other mammals. The method of the present invention produces a self-microemulsifyable base composition containing concentrations of bio-available CoQ10 of up to about 20% by weight of the composition. The base composition can then be utilized in the production of supplements and/or agents that are administered orally in a capsule or liquid formulation; parenterally in an intravenous or intramuscularly formulation; topically in a lotion, cream or salve formulation; or ophthalmically in an eye drop formulation. For each of these formulations, the preferred base composition consists essentially of: CoQ10 included in the composition in an amount of about 2% to about 20% by weight of the composition; a water-immiscible solvent included in the composition in an amount of up to about 30% of the composition; and a non-ionic surfactant, containing polyethylene glycol, included in the composition in an amount of about 60% to about 82% by weight of the composition. Preferably, a predetermined amount of the water-immiscible solvent is first heated to a preparation temperature of about 27° C. to about 40° C. and then a predetermined amount of the high purity crystalline CoQ10 is stirred into the heated solvent. The mixture of solvent and CoQ10 is stirred until all of the CoQ10 crystals are completely dissolved into the solvent. While maintaining the temperature of the solvent and CoQ10 at about the preparation temperature, a predetermined amount of the non-ionic surfactant, which can be pre-heated to the preparation temperature, is then added to the solvent and dissolved CoQ10, under sufficient stirring in order to create a self-microemulsifyable base composition, which is anhydrous, homogenous, thermodynamically stable, and appears as an orange-colored, transparent liquid, a characteristic of CoQ10 solutions.

For the capsule formulation, a unit dosage from the base composition is then added to a dissolvable capsule, preferably a soft gelatin capsule, in order to form an orally administrable CoQ10 nutritional supplement. When a capsule containing the self-microemulsifying composition enters the digestive tract, the temperature of the body's digestive juices warms the composition, causing any of the CoQ10 that may have re-crystallized out of the composition to become re-dissolved into the composition before the capsule dissolves. The re-dissolution of CoQ10, which occurs at body temperature, ensures that more of the CoQ10 is bioavailable when the capsule dissolves. Upon dissolution of the capsule, the self-microemulsifying composition comes into contact with the digestive juices and naturally forms micellar-type bioavaible microemulsions, consisting of micelles containing CoQ10 with each micelle having a diameter of about 12 to 25 nanometers.

In addition to preparing the orally administrable CoQ10 supplement in capsule form, the base composition of the present invention can be used in the preparation of a CoQ10 containing beverage or mouthwash. For the beverage, it is preferable that one (1) part of the base composition is diluted with two (2) parts of water, having a temperature of about 40° C. to about 50° C., in order to form a microemulsion. After the microemulsion cools down to room temperature, a predetermined amount of the microemulsion can be added to a consumable drink or liquid in order to form the CoQ10-containing beverage. For the mouthwash, a predetermined amount of the undiluted base composition can be added directly to a water-based mouthwash.

The present invention further includes the preparation of a topically administrable CoQ10 supplement in which the base composition can be used directly as a lotion, cream or salve.

Further, the base composition of the present invention can be used in the preparation of parenterally administered agents. For intramuscular applications a predetermined amount of the base is injected directly into the muscle, where the base forms a bioavailable microemulsion in the extracellular fluids. For intravenous and ophthalmic applications a predetermined amount of the base is added to a carrier liquid in an amount of about one (1) part of the base to about three (3) to four (4) parts of the carrier liquid and the bioavailable microemulsion forms in the carrier liquid, which can then be injected intravenously for the intravenous application, or applied topically for the ophthalmic application.

Finally, the present invention includes a solvent-free base composition which is also suitable for use in the production of supplements and/or agents that are administered orally in a capsule or liquid formulation; parenterally in an intravenous or intramuscularly formulation; topically in a lotion, cream or salve formulation; or ophthalmically in an eye drop formulation. The solvent-free microemulsifyable base composition consisting essentially of: CoQ10 included in the composition in an amount of about 2% to about 3% by weight of the composition; and a liquid or molten non-ionic surfactant, containing polyethylene glycol, included in the composition in an amount of about 97% to about 98% by weight of the composition.

DETAILED DESCRIPTION OF THE INVENTION

The present invention generally provides a method and a composition for enhancing the dissolution and bioavailable properties of CoQ10 nutritional supplements and/or therapeutic agents for a human being and other mammals. The method of the present invention produces a self-microemulsifyable base composition containing concentrations of CoQ10 of up to about 20% by weight of the composition. The base composition can then be utilized in the production of supplements and/or agents that are administered orally in a capsule or liquid formulation; parenterally in an intravenous or intramuscularly formulation; topically in a lotion, cream or salve formulation; or ophthalmically in an eye drop formulation. For each of these formulations, a preferred base composition consists essentially of: CoQ10 included in the composition in an amount of about 2% to about 20% by weight of the composition; a water-immiscible solvent included in the composition in an amount of up to about 30% of the composition; and a non-ionic surfactant, containing polyethylene glycol, included in the composition in an amount of about 60% to about 82% by weight of the composition.

The preferred method of producing a self-microemulsifyable base composition consists essentially of heating a predetermined amount of the solvent to a preparation temperature of about 27° C. to about 40° C. and then a predetermined amount of the microcrystalline CoQ10 is stirred into the heated solvent. The mixture of solvent and CoQ10 is stirred sufficiently until all of the CoQ10 crystals are completely dissolved into the solvent, as indicated by a change in the appearance of the mixture from a yellowish-colored, opaque liquid into an orange-colored, transparent liquid. Depending upon the type of surfactant and solvent being used, the quantity of CoQ10 being dissolved and the preparation temperature, the time needed to dissolve the CoQ10 can take from a few minutes up to several hours. While maintaining the temperature of the solvent and CoQ10 at about the preparation temperature, a predetermined amount of the non-ionic surfactant, which can be pre-heated to the preparation temperature, is then added to the solvent and dissolved CoQ10, under sufficient stirring in order to create a self-microemulsifyable base composition, which is anhydrous, homogenous, thermodynamically stable, and appears as an orange-colored, transparent liquid, a characteristic of CoQ10 solutions. Generally, the CoQ10, solvent, and surfactant elements must be stirred for only about three (3) to five (5) minutes in order to form the self-microemulsifyable base composition.

Alternatively, in addition to the preferred method of preparing the self-microemulsifyable base composition, the base composition can be prepared by mixing a predetermined amount of the water-immiscible solvent with a predetermined amount of a molten or liquid form of the non-ionic surfactant. The mixture is stirred for about three (3) to about five (5) minutes. Then, while maintaining the preparation temperature of the mixture at about 27° C. to about 40° C., a predetermined amount of a microcrystalline form of CoQ10 is added to the mixture under sufficient stirring, about ten (10) to about thirty (30) minutes, until all the CoQ10 dissolves, as indicated by a change in the appearance of the mixture from a yellowish-colored, opaque liquid into an orange-colored, transparent liquid. The resulting self-microemulsifyable base composition has the same properties as the base composition prepared in accordance with the preferred method: a thermodynamically stable solution of CoQ10, which is anhydrous, homogenous, and appears as an orange-colored, transparent liquid.

In yet another alternative, the base composition can be prepared by combining in a single step: a predetermined amount of a microcrystalline form of CoQ10; a predetermined amount of the water-immiscible solvent; and a predetermined amount of a molten or liquid form of the non-ionic surfactant. Then, while maintaining the preparation temperature of the elements at about 27° C. to about 40° C., the self-microemulsifyable base composition is formed by stirring the elements for about ten (10) to about thirty (30) minutes until all of the CoQ10 dissolves, as indicated by a change in the appearance of the mixture from a yellowish-colored, opaque liquid into an orange-colored, transparent liquid. Again, the end result is the same as that in the preferred embodiment: a self-microemulsifyable base composition, which is thermodynamically stable, anhydrous, homogenous, and appears as a an orange-colored liquid, transparent liquid.

The highest concentration of CoQ10 of about 20% by weight of the base composition is obtained by using a water-immiscible solvent that is capable of dissolving an amount of CoQ10 that is approximately equal to the weight of the solvent, and by preparing the base at a preparation temperature of about 37° C. to about 40° C., which results in a base composition that is a thermodynamically stable solution at about the body temperature of a human being and most other mammals. The base composition exhibits thermodynamic stability because, even for concentrations of CoQ10 of about 20% by weight of the base, the CoQ10 is completely dissolved into the base when the base is at a temperature of about 35° C. to about 40° C. The present invention utilizes this important characteristic of the base composition to produce nutritional supplements and therapeutic agents that contain concentrations of bioavailable CoQ10 of up to about 20% by weight of the base.

In order to utilize the self-microemulsifyable base composition in the production of a capsule formulation of the present invention, a unit dosage from the base, which has been prepared in accordance with the preferred method or in accordance with either of the two (2) alternate methods, is simply added to a dissolvable gelatin capsule which can be stored until ready for use. However, for a capsule containing a base composition that was prepared at a temperature of about 37° C. and contains a concentration of CoQ10 of about 20% by weight of the base, during storage of the capsule at a temperature below about 37° C., for example at room temperature, some of the CoQ10 will most likely re-crystallize out of the base composition. It is an important characteristic of the present invention, however, that the re-crystallized CoQ10 is composed of microcrystals that are well dispersed within the base. As a result, when a capsule is ingested and it comes into contact with the watery digestive tract contents, having a temperature of about 37° C. or higher, the re-crystallized CoQ10 re-dissolves into the liquid base before the capsule wall breaks down, normally taking about three (3) to ten (10) minutes after the capsule is ingested. The re-dissolving of CoQ10 ensures that more of the CoQ10 is bioavailable when the capsule is disrupted, allowing the liquid base composition to come into contact with the watery contents of the digestive tract. Upon dissolution of the capsule, the self-microemulsifyable base composition, containing CoQ10 which is fully dissolved in the base, comes into contact with the watery digestive juices, and the base naturally forms micellar-type, bioavailable microemulsions. These micellar microemulsions consist of micelles containing CoQ 0, with each micelle having a diameter of about 12 to about 25 nanometers. Further, the micellar microemulsions formed by the described invention form typically optically clear micellar dispersions in water. A typical micellar particle formed might contain only about 300 molecules of surfactant, 150 molecules of CoQ10, and 1000 molecules of solvent.

When a capsule containing a concentration of CoQ10 of about 20% by weight of the base, which is a thermodynamically stable solution at body temperature, is stored at a temperature below body temperature, for example at room temperature, some of the CoQ10 may re-crystallize as yellow-colored CoQ10 microcrystals, will cause the transparent, orange-colored liquid composition to become yellow and opaque. Although the change in appearance does not adversely impact on the ability of the CoQ10 crystals to re-dissolve into the composition, in some supplements or agents it might be desirable to prevent the change in appearance. This result can be accomplished by simply reducing the concentration of CoQ10 in the composition by about 25%, and preferably increasing the concentration of the solvent by about 8%. At this lower concentration level, which is still about 3 times higher than concentration levels previously obtainable using prior techniques, the CoQ10 does not re-crystallize out of the base at room temperature, approximately 23° C.; rather, the CoQ10 remains dissolved in the base, which does not change in appearance.

The inventors have further found that by preparing the self-microemulsifyable base composition in accordance with either the preferred preparation method or by using one of the two alternative preparation methods, that the total time needed to prepare the base can be substantially reduced at preparation temperatures above 37° C. The speed at which the CoQ10 dissolves into the solvent is primarily a function of the temperature of the solvent and its viscosity, but the base composition that is prepared at a temperature above 370 will have the same properties as a base prepared at a temperature of 37° C. If CoQ10 crystals are added to solvents hot enough to melt CoQ10 (48° C. to about 52° C.) the molten CoQ10 mixes and dissolves almost immediately. On the other hand, under room temperature conditions, several hours of stirring may be required to obtain even a 5% CoQ10 concentration in a highly viscous solvent such as a triglyceride oil. By contrast, a low viscosity solvent, such as sweet orange oil can dissolve a 30% CoQ10 concentration under room temperature almost immediately. The fact that CoQ10 melts at about 48° C. to about 52° C. and then is soluble at high concentrations in a wide range of only modestly hydrophobic media, such as ethanol, is distracting to the design of high concentration CoQ10 solutions at room temperature or body temperature. Many different high concentration solutions of CoQ10 which form readily at the high temperatures of molten CoQ10 are not stable, or are meta-stable, at body temperature. It is a specific feature of the present invention, however, that the preparation temperature does not need to be increased to the melting point of CoQ10, which is approximately 48° C. to 52° C. for high grade crystalline CoQ10.

Although the present invention discloses that the base composition must be prepared at a preparation temperature at or slightly above body temperature in order to obtain a CoQ10 concentration of about 20% by weight of the base, the invention also includes preparation temperatures below body temperature, down to about 27° C. If the same solvent and surfactant that were used to prepare the 20% CoQ10 concentration are also used to prepare the base at a temperature below body temperature, then the concentration of CoQ10 must be reduced by a predetermined amount in order to ensure that all of the CQ10 dissolves into the base composition, or if any of the CoQ10 re-crystallizes out of the base at a temperature below the preparation temperature, to ensure that the crystals will re-dissolve into the base when the composition temperature returns to its preparation temperature.

Additionally, it will be apparent to those skilled in the art that a concentration of CoQ10 above 20% can be added to the base composition without departing from the teachings of the present invention. The higher CoQ10 concentration, however, will not translate into a higher concentration of CoQ10 being bioavailable in a microemulsion which forms in the gastrointestinal tract, because the increase in the concentration of CoQ10 necessarily requires a corresponding reduction in the concentration of the surfactant. A reduction in the amount of surfactant will similarly reduce the number of micelles containing CoQ10 within the microemulsion and, consequently, will reduce the concentration of CoQ10 that is bioavailable within the intestinal tract.

The capsule formulation of the present invention discloses a base composition containing a non-ionic surfactant, containing polyethylene glycol (hereinafter generally referred to as a "PEG-containing surfactant"), which is completely miscible with water, meaning that the surfactant has a high affinity for and readily dissolves in water, where the surfactant forms an optically clear micellar solution. It is this characteristic of forming a micellar solution that causes the solubilized composition of surfactant and CoQ10, either with or without a water-immiscible solvent, to form a micellar microemulsion in water.

Generally, the inventors have discovered that PEG-containing surfactant molecules that form acceptable CoQ10 microemulsions in water are characterized by surfactant molecules in which the total length of the polyethylene glycol portion of each surfactant molecule, whether linear or non-linear, is from 2 to 6 times longer than the length of the hydrophobic hydrocarbon portion of the molecule. A decrease in this ratio to below 2 typically produces surfactants that do not form micellar solutions in water, nor do the surfactants form CoQ10 microemulsions, although the surfactants may form ordinary emulsions. A value above 6 in the ratio of the length of the polyethylene glycol portion to the hydrophobic portion of the surfactant molecule will allow both micellar solutions and microemulsions to form, but will also increase the viscosity and melting point of the surfactant, substantially increasing the time needed to prepare the base composition. This higher ratio will also reduce the loading factor of the surfactant, which is defined as the amount of CoQ10 or hydrophobic solvent that given weight of surfactant is able to solubilize into water in order to form a clear microemulsion.

The most acceptable PEG-containing surfactants for use as CoQ10 solubilizers in the capsule formulation share some common features: 1) they are non-ionic and depend on PEG (polyethoxy) components for their high affinity for and solubility in water; 2) the hydrophobic R group(s) of the surfactant must be bio-compatible and have a melting point close to or below body temperature, and 3) the PEG chain or chains attached to one end of the R group(s) must be long enough in total to limit the size of surfactant micellar aggregates in water. This last feature ensures that the small micellar aggregates (or optically clear microemulsions which resemble micellar aggregates in scale) that form in water are thermodynamically stable. Typically, the cloud point concentration of the preferred pure surfactants in water is very high or nonexistent.

More specifically, the most preferred PEG-containing surfactant for use in the preparation of the base composition for the capsule formulation of the present invention can be defined as belonging to one of two classes. A first class of PEG-containing surfactant has general structure of [POE(n)] subm-R'—R; where POE is a polyoxyethylene moiety (also known as a polyethylene glycol or PEG moiety) of -mer number n, and having m of these POE functional groups attached to R'; where the value of m is one to three; where R' is a linking moiety, particularly glyceryl, sorbitan, ester, amino, or ether (oxygen) functions; and where R is a hydrophobic moiety consisting of saturated or unsaturated alkyl or alkylphenyl groups. Examples of non-ionic surfactants within this first class are polyoxyethylene monoalkyl ethers, polyoxyethylene alkylphenols, polyethylene glycol fatty acid monoesters, polyethylene glycol glycerol fatty acid esters, polyoxyethylene sorbitan fatty acid esters, and polyoxyethylene sterols. Mixtures of any of these chemical moieties also function as good surfactants for the purposes of the invention.

A useful and preferred subclass within the first class of PEG-containing surfactants includes surfactants having a structure further defined by a ratio of A, which is the total number of POE -mer units in the surfactant (given by the product of -mer number n and total PEG chain number m per molecule), to B, which is the number of carbons in the hydrophobic functional group R, is between about 0.7 and 4; preferably with A/B being in the range from about 1 to 2. Examples of non-ionic surfactants within this subclass are PEG-15 monolaurate, PEG-20 monolaurate, PEG-32 monolaurate, PEG-48 monolaurate, PEG-13 monooleate, PEG-15 monooleate, PEG-20 monooleate, PEG-32 monooleate, PEG-72 monooleate, PEG-15 monostearate, PEG-660 15-hydroxystearate (BASF Corporation "Solutol®"), PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate (polysorbate 80, Tween 80), PEG-20 sorbitan monolaurate (Tween 20), PEG-20 sorbitan monopalmitate (Tween 40), and PEG 20 sorbitan stearate (Tween 60), PEG-40 sorbitan monooleate, PEG-80 sorbitan monolaurate, POE-23 lauryl ether, POE-20 oleyl ether, PEG 30-60 nonyl phenol series (Triton N series), PEG 30-55 octyl phenol series (Triton X series, particularly X-305 (POE 30) and X-405 (POE 40). Mixtures of any of these surfactants also function well.

A second class of PEG-containing surfactants is derived from triglyceride oils, and has general structure of [R'-(POE) subn]sub3-glyceride, where POE is a polyoxyethylene moiety (also known as a polyethylene glycol or PEG moiety) of -mer number n, inserted between fatty acid acyl residues R' and a glycerol residue (glyceride), which had, before polyethoxylation, been attached directly to the acyl residues as a common triglyceride. Examples of non-ionic surfactants within this second class are the polyoxyethylated vegetable oils, such as polyethoxylated corn oil or polyethoxylated castor oil. Mixtures of these polyoxyethylated vegetable oils also function as good surfactants for the purposes of the invention.

A preferred subclass within the second class of PEG-containing surfactants includes surfactants having a structure further defined by a ratio of A, which is the total number of POE -mer units in the surfactant (given by the product of -mer number n and total PEG chain number 3 per molecule), to B, which is the number of carbons in the 3 fatty acid R', residues, is between about 0.5 and 3; preferably with A/B being in the range from about 0.6 to 1.5. Examples of non-ionic surfactants within this subclass are PEG-40 palm kernel oil, PEG-50 hydrogenated castor oil, PEG-40 castor oil, PEG-35 castor oil (e.g., Cremaphor®-35), PEG-60 castor oil, PEG-40 hydrogenated castor oil, PEG-60 hydrogenated castor oil, and PEG-60 corn oil. Mixtures of these surfactants also function well for purposes of the invention.

A third class of PEG-containing surfactants, analogous to the two above, can in theory be manufactured by polyethoxylation of diester compounds consisting of fatty acid esters of biocompatible dialcohols, such as propylene glycol. The inventors expect that these compounds will have properties substantially the same as those described in the first two classes of PEG-containing surfactants, so long as the ratio of residue R fatty acid carbons and PEG mer-number is maintained between 0.5 to 4.

Finally, it is noted that mixtures of the two chemically defined classes of PEG-containing surfactants also function well in the present invention. All of the preferred PEG-containing surfactants are compatible and function well when used as mixtures, but it is a feature of the invention that particular mixtures are not needed or preferred, and preferred surfactants have been chosen to work as single agents in production of microemulsions, in contrast to prior inventions which specify certain surfactant mixtures aimed at attaining particular "HLB" (hydrophobic lipophilic balance) ratios for a mixture of 2 or more surfactant types.

Adding a preferable PEG-containing surfactant (for example BASF Corporation's Solutol® which forms "solutions" of up to 30% Solutol® without a great increase in viscosity) to water, causes formation of a micellar solution of self-aggregated surfactant clusters of diameter of about 12 nm. The solution forms an optically clear dispersion, analogous to a microemulsion, but technically not a microemulsion because the solution contains only one component other than water. With the addition of a hydrophobic guest solute, like CoQ10 or a hydrophobic CoQ10 solvent like d-limonene or ethyl oleate (described below), such micellar solutions are generally described as "microemulsions". It is questionable, however, whether the molecular structure is always that of the classical two-component lipid-in-water emulsion, containing a tiny droplet of hydrophobic substance "coated" with surfactant. Doppler light scattering studies done by the inventors show that the microemulsions formed from all classes of surfactants described in the present invention have diameters as small as 12 nm (120 Angstroms), meaning the particle radius is just less than the length of a single uncoiled surfactant molecule (about 7 nm). Such small and simple structures have no room for a classical emulsion hydrophobic liquid drop core, but must contain their embedded solvents and hydrophobic guest molecules (like CoQ10) in a relatively jumbled core, closely interwoven by the hydrophobic heads of the surfactant ensemble, which are interlocking and probably touching from opposite sides of the micelle. For example, the inventors have found no difference in the diameter of "empty" aggregates in simple micellar solutions of Solutol®, and the "microemulsion" particles which are formed when Solutol® forms microemulsions with hydrophobic solvent guest molecules like ethyl oleate.

An important property of the base composition of the present invention that contains a concentration of CoQ10 of about 20% by weight of the base is that the base is thermodynamically stable solution of CoQ10 at a temperature of about 37° C. or higher, which includes the body temperatures of a human being and most other mammals. Accordingly, the PEG-containing surfactants, described above, that are acceptable for use in preparing the base composition containing a 20% CoQ10 concentration are selected, in part, in order to ensure that the base is a stable solution at body temperature. In this regard, it is preferable that the water-immiscible CoQ10 solvent that is selected for use in preparing the base also contribute to the formation of a base that is thermodynamically stable at body temperature. Solvents that satisfy these criteria are sometimes referred to in the literature as "co-solvents," in that the solvent cooperates with the surfactant to form a base having the desired property. However, the inventors have found that using the preferred group of non-ionic surfactants, by far the most important interaction of the solvent is directly with the CoQ10, to keep it from crystallizing out of the base.

Primary considerations in the choice of an acceptable water-immiscible solvent are somewhat similar to those in choosing an acceptable surfactant. In addition to the basic requirements of bio-compatibility, low toxicity and good taste and odor, the solvent must have a melting point at or about the temperature of a human and most other mammals (about 37° C.), and be able to dissolve a substantial amount of CoQ10 below body temperature. Triglyceride oils in general do not fulfill these criteria because of the difficulty in dissolving more than about 5% CoQ10 by weight into them at body temperature. Because CoQ10 is prone to re-crystallize from most of the common bio-compatible solvents (vegetable oil, MCT, tributyrin, ethanol, propylene glycol, Span-80, etc.), the main challenge in constructing high concentration CoQ10 microemulsion bases is to find a pleasant-smelling biocompatible hydrophobic solvent that is able to dissolve high concentrations of CoQ10 at or about body temperature. Once such a solvent is identified, the saturation capacity of the solvent with CoQ10 at body temperature is then determined, and a reduction in the concentration of CoQ10 is made to ensure that mixture of the CoQ10 and solvent, along with the more hydrophilic surfactant, will not cause CoQ10 precipitation. Typically, in order to avoid CoQ10 precipitation, the CoQ10 concentration needs to be reduced by about 10%. After the appropriate concentration of CoQ10 in solvent is produced, the preferred group of PEG-containing surfactants can then be used in appropriate proportion to form microemulsion bases, and self-microemulsifying systems, with such CoQ10 solvent solutions.

Acceptable water-immiscible biocompatible solvents for use in the present invention can be generally selected from one of three (3) groups of esters: monoesters, diesters, and triesters. The esters are formed from a group of liquids composed of aliphatic (saturated and unsaturated; straight and branched chain) acid or alcohol residues. The monoesters are composed of residues from mono-alcohols and mono-acids. The diesters are composed of residues from mono-acids and di-alcohols, or from di-acids and mono-alcohols. The triesters are composed from mono-acids and tri-alcohols, or from tri-acids and mono-alcohols.

For the monoesters, the preferred saturated or unsaturated aliphatic acid residues are selected from the group containing acetic, propionic acid, or other saturated or unsaturated biocompatible aliphatic acids. Fatty acids with an even number of carbons of length Csub8 or longer are preferred, due to unpleasant taste and odor of short chain fatty acids and ester preparations which contain them. The saturated or unsaturated aliphatic alcohol residue for the ester is preferably selected from the group containing ethyl, n-propyl alcohol, or other saturated or unsaturated biocompatible aliphatic alcohols. Many such alcohols are straight-chain mono-alcohols of eight or more carbons, such as n-octanol. Alkyl alcohols with an even number of carbons are preferred. Preferred examples of monoester solvents are ethyl oleate, propylene glycol dicaprylate, isopropyl myristate, ethyl laurate, butyl oleate, oleyl acetate, oleyl propionate, octyl octanoate, octyl decanonate, and oleyl oleate.

Preferred diesters are also selected due to biocompatibility of the alcohols and carboxylic acids derived from the ester residues, as well as choice of residues to formulate an ester which is liquid at near body temperature. Each residue will preferably correspond to a carboxylic acid or alcohol which is biocompatible. A diester may be composed of two carboxylic acid residues condensed with one di-hydroxy alcohol, or one di-carboxylic acid residue with two mono-alcohols.

For diesters derived from di-alcohols and mono-acids, the preferred di-alcohol is selected from the group of biocompatible small di-hydroxy alcohols, such as propylene glycol, 1,2 butane diol, and 1, 3 butanediol. The preferred aliphatic mono-acids are selected from the group which contains acetic or propionic acid, or the aliphatic acids which are fatty acids with an even number of carbons of length Csub8 or longer. Preferred examples of such liquid diesters based on di-alcohols and mono-acids are propylene glycol dilaurate, propylene glycol dioleate, propylene glycol dicaprylate, and 1, 2 butane glycol dioleate.

For diesters derived form di-acids and mono-alcohols, the di-acids can generally be selected from the group of di-carboxylic acids, in which the aliphatic acid residues are biocompatible aliphatic, saturated or unsaturated di-carboxylic acids, such as succinic acid, fumaric acid, malic acid, malonic acid, glutaric acid, 2-oxoglutaric acid, or longer chain dicarboxylic acids such as sebacic acid. For diesters derived from mono-alcohols, the mono-alcohols for use with short dicarboxylic acids (such as succinic acid, fumaric acid, malic acid, malonic acid, glutaric acid, 2-oxoglutaric acid) are selected from the group of biocompatible monohydroxy alcohols of 10-carbons or longer, with particular attention to capryl alcohol and oleyl alcohol as forming esters with adequately low melting points but also adequately low tissue irritative qualities and acceptable taste. This generally requires esters with a total carbon number of 16 or more. Preferred examples of such liquid diesters based on di-acids and mono-alcohols are dioleyl fumarate, dioleyl malonate, and di-propyl sebacate. Mixed esters such as capryl oleyl succinate are also suitable.

The biocompatible triesters can be composed of residues of biocompatible tri-alcohols, such as glycerol, and mono-acids. Alternatively, triesters can also be made from the esters of biocompatible tricarboxylic acids, such as citric and isocitric acid, and monoalcohols. Preferred tri-alcohol triesters include the liquid natural triglycerides, and other synthetic triglycerides. These triglycerides include, but are not restricted to, glycerol trioleate, medium chain triglyceride oil, and mixed glyceride esters in which acyl groups derived from caprylic and oleic acid, are preferred. The corresponding liquid triesters derived from tricarboxylic acid esters and monoalcohols include, but are not restricted to, tricapryl citrate, trioleyl citrate, tricapryl isocitrate, trioleyl isocitrate, and mixed alcohol esters of citric and isocitric acid.

Additionally, water-immiscible biocompatible solvents for use in the present invention can be generally selected from the group of liquid plant essential oils (which are not triglycerides). More specifically, the solvents can be selected from the group of: 1) terpenoid-based liquid plant essential oils, containing as primary ingredients monoterpenes (such as limonene and myrcene), or sesquiterpenes (such as cedrene or farnescene); 2) terpenoid ketone-based liquid plant essential oils, such as carvone based essential oils (e.g. spearmint oil, kuromoji oil), fenchone-based oils (e.g. fennel oil), or camphor-based oils (e.g. rosemary oil); 3) plant essential oils containing terpenoid alcohols (such as linalool, geraniol, citronellol, or farnesol), and their derivatives, (such as acetate, butyrate, benzolate, anthranylate); 4) plant essential oils containing terpenoid aldehydes (such as citral, citronellal, or geranial); 5) citrus-derived essential plant oils, including but not limited to, eau de brouts oil, petigraine oil, neroli oil, and bitter orange oil (all from *Citrus aurantium*), sweet orange oil (the expressed oil of *Citrus sinensis*, which is preferred), lime oil, grapefruit oil, lemon oil, tangerine oil, mandarin oil (*C. reticulata*), tangelo (*C. reticulata×C. paradisi*) oil, or other citrus essential oils; 6) non-citrus biocompatible liquid plant essential oils, including but not limited to, essential oils of Abies Alba, ale (various pine species), ambrette seed, angelica seed, benzoin (*Styrax benzoin*), bergamot (*C. bergamia*), bergamot mint (*M. citrata*), cabreuva, cananga, carrot seed, cascarilla, Atlas cedarwood (*C. atlantica*), Texas cedarwood (*J. mexicana*), Virginian cedarwood (*J. virginiana*), celery seed, German camomile (*C. recutita*), Roman Camomile (*A. nobilis*), citronella (*C. nardus*), French clary sage (*S. sclarea*), copaiba, cuceb, cypress, davana, deertongue, fenugreek, Canadian fir needle (*A. balsamea*), galbanum, geranium (*P. graviolens*), ginger, gurjun, hay, hibawood, immortelle, jasmine, juniperberry, labdanum, lavandin, lavender, lemongrass (*C. citratus* or *C. flexosis*), linaloe, Spanish marjoram (*T. masticina*), may chang, mimosa, myrtle, palmarosa, patchouli, black pepper, Peru balsam, Peruvian pepper (*S. molle*), Phoenecian juniper (*J. phoenicea*), Scotch pine (*P. sylvestris*), Bulgarian or Moroccan rose (*R. damascena*), rosemary, Spanish sage (*S. lavandulaefolia*), snakeroot, spearmint, hemlock spruce oil (containing *T. canadensis, P. mariana, P. glauca*), turmeric, ylang-ylang; 7) absolute (i.e., solvent extracted) plant oils, including but not limited to, broom oil (*S. junceum*), mastic oil (*P. lentiscus*), verbena oil (*L. citriodora*), narcissus oil, orange flower oil, cabbage rose oil (*R. centifolia*), tobacco leaf oil (*N. affinis*); and 8) purified biocompatible chemicals found in plant essential oils, in particular d-limonene (which is preferred), l-limonene, d-carvone, l-carvone, l-linalyl acetate, l-linalool, geranyl acetate, farnesol, farnesyl acetate, and other chemically related bio-compatible water-immiscible liquid terpenoids (mono and sesquiterpenoids), terpenoid ketones, terpenoid alcohols, terpenoid alcohol esters, and terpenoid aldehydes.

Lastly, water-immiscible biocompatible solvents for use in the present invention can also be selected from the group of benzoic acid esters of ethanol, n-propanol, isopropanol, and benzyl alcohol.

It will be apparent to those skilled in the art that in addition to the solvents described above, any of the solvents can be mixed with any of the other solvents without deviating from the scope of the present invention.

As an example of the present invention's ability to produce a fully dissolved CoQ10 concentration of about 20% by weight of the base composition for use in the capsule formulation, it is most preferable to use sweet orange oil, containing the active ingredient d-limonene, as the water-immiscible, biocompatible solvent for CoQ10. By using this solvent, thermodynamically stable concentrations of CoQ10 up to about 55% are possible at body temperature. Because a preferred surfactant like Cremophor®-35 is able to solubilize up to 66% of its weight in lipophilic solution (i.e., to a final mixture of 60% surfactant, 40% hydrophobe mix of CoQ10/solvent), it follows that 6 parts of Cremaphor® can be used to solubilize 4 parts of 50% CoQ10 liquid solution to form a stable microemulsion base, which is 20% CoQ10 by weight. This base in turn is a self-microemulsifying system in water at 37° C. When using sweet orange oil as the solvent, a reduction in the CoQ10 concentration to about 50% is sufficient to inhibit precipitation from the base composition at a temperature at or above 37° C.

The present invention is readily distinguished from previous methods that have been utilized in the preparation of emulsion bases, in that formulation of the present invention does not include the use of water-soluble alcohols or polyalcohols, such as ethanol, propylene glycol, n-propanol, glycerol, t-butanol, and the like. Some discussion of these is in order. The role of these substances in emulsion bases for very lipophilic substances like CoQ10 is not that of a primary solvent or even "co-solvent", since even though such hydrophilic alcohols may dissolve large amounts of CoQ10 at the melting temperature of CoQ10, they are nevertheless very poor solvents for CoQ10 at temperatures characteristic of biologic systems. Instead, the role of such alcohols in pre-emulsion bases is not that of a chemical solvent, but rather that of a small molecule which acts to thin the emulsion base and simulate the effect of heat, by decreasing the emulsion base viscosity. Alcohols may also prepare the surfactant system for the entry of water to form the emulsion, by pre-interacting with the hydrophilic portions of surfactant molecules to separate them. However, the inventors of the present invention have determined that once these emulsions, or micellar microemulsions, form, then such small water-soluble alcohols no longer play a role in their thermodynamic stability. Accordingly, once the emulsion or microemulsion has been formed, the alcohol may be dispensed with, and if an emulsion can be formed without aid of alcohol, then alcohol does not enhance CoQ10 concentration or stability in the emulsion. Therefore, the inventors have disclosed the importance of carefully chosen biocompatible PEG-containing surfactants, all of which have a relatively high affinity for water, as well as low viscosity, to allow excellent mixing with water at the relatively low production temperatures described in the invention. Thus, the inclusion of small molecular weight alcohols is not necessary for any stage in the formation of CoQ10 emulsions or microemulsions from the surfactant, even at relatively low temperatures such as room temperature or body temperature.

In addition to providing a capsule formulation containing CoQ10 concentrations of up to 20% by weight of the composition, the method and composition of the present invention includes a capsule formulation which includes a CoQ substance other than CoQ10. Specifically, the capsule formulation also includes using any of the following CoQ substances: CoQ1, CoQ2, CoQ3, CoQ4, CoQ5, CoQ6, CoQ7, CoQ8, or CoQ9 (hereafter referred to individually as a "CoQ substance" and collectively as "CoQ substances"). The same methods of preparation can be utilized as those methods used in connection with the capsule formulation containing CoQ10, with the only difference being that the range of concentrations of Co10 specified in the preferred embodiment are replaced with the same range of concentrations of one of the CoQ substances. Further, any of the PEG-containing surfactants and water-immiscible solvents disclosed for use in the preparation of the CoQ10 base composition for the capsule formulation can be used to prepare the base containing any of the CoQ substances; however the preferred PEG-containing surfactant is PEG-35 castor oil, and the preferred water-immiscible solvent is sweet orange oil. The resulting base composition, containing any one of the fully-dissolved CoQ substances, has the same characteristics as the base composition containing CoQ10, in that the self-microemulsifyable base composition is a thermodynamically stable solution, which is anhydrous, homogenous, and appears as a orange-colored, transparent liquid. Similarly, a unit dosage from the composition can be added to a dissolvable capsule, preferably a soft gelatin capsule, in order to form an orally administrable nutritional supplement containing a CoQ substance. Upon dissolution of the capsule within the digestive tract, the base composition containing the fully-dissolved CoQ substance comes into contact with the digestive juices and naturally forms a micellar-type, highly-bioavailable microemulsion.

In addition to the orally administrable CoQ10 nutritional supplement that is prepared in capsule form, the present invention includes a CoQ10 nutritional supplement that can be orally administered in a liquid formulation as a CoQ10-containing beverage or a mouthwash. Generally, the liquid formulation is provided by using the preferred base composition of the present invention and dispersing a predetermined amount of the base composition into a consumable liquid or drink in order to create the CoQ10-containing beverage. For this purpose, the base composition is prepared by using the same preferred method that is used to prepare the base composition for use with the dissolvable capsule formulation, or by using either of the two alternative methods for preparing the base for use with the dissolvable capsule formulation. In one embodiment of the liquid formulation, CoQ10 is included in the base in an amount of about 15% by weight of the base, the PEG-containing surfactant included in the base in an amount of about 60% by weight of the base, and the water-immiscible solvent included in the base in an amount of about 25% by weight of the base. Although any of the previously disclosed surfactants and solvents that can be used to prepare the base composition for the capsule formulation are acceptable for use in the preparation of the liquid formulation, the preferred surfactants for use with the liquid form of the present invention are PEG-660 15-hydroxystearate (BASF Corporation's Solutol®), PEG-15 monooleate, PEG-23 monostearate or PEG-23 monomyristate, because of their acceptable taste and odor. Further, the most preferred solvents are sweet orange oil and other essential citrus oils because of their biocompatibility and acceptable taste. Other acceptable solvents are esters, such as ethyl oleate, isopropyl myristate, or propylene glycol dicaprylate, also because of their biocompatibility and acceptable taste. A higher concentration of CoQ10 can be dissolved in citrus oil solvent based compositions, than can be dissolved in ethyl oleate based compositions. In order to make the CoQ10-containing beverage, in one embodiment one (1) part of the base composition containing the concentrations set forth above is first diluted with about two (2) parts of about 40° C. to about 50° C. water; then the diluted mixture is stirred for about five (5) to ten (10) minutes in order to form a warm microemulsion. After the microemulsion cools down to room temperature, a predetermined amount of the microemulsion can be added to a consumable drink or liquid, which can be a water-based drink or even an alcohol-based drink of up to 80 proof, in order to form the CoQ10-containing beverage. In another use, a predetermined amount of the undiluted base composition can be added directly to a water-based mouthwash, and after sufficient stirring a microemulsion forms in the mouthwash.

The liquid formulation of the CoQ10-containing microemulsion can be included in the beverage such that the CoQ10 is in a concentration of an amount of up to about 10% by weight of the beverage, and exhibit good stability at room temperature, although such high concentrations of CoQ10 in commercial use might present problems due to gastrointestinal laxative properties of the PEG-containing surfactants at doses above 10 grams or more. However, a similar limitation in the amount of base composition that can be included in a mouthwash, where the base forms a microemulsion, is not needed because insufficient amounts of the mouthwash enter the gastrointestinal tract. For the liquid formulation, esters such as ethyl oleate, isopropyl myristate or propylene glycol dicaprylate may be used freely as solvents for making the base composition, but traditional essential plant oil practice suggests limiting ingestion of essential citrus oils to less than about a gram a day.

The present invention can further be used to provide a topical formulation in which the preferred base composition of the present invention can be applied directly to the skin as, for example, a lotion, cream or salve. For the topical formulation, it is most preferable to use CoQ10 in a reduced form (i.e. ubiquinol). Again, although any of the previously disclosed PEG-containing surfactants and water-immiscible solvents that can be used to prepare the base composition for the capsule formulation are acceptable for use in the preparation of the topical formulation, the preferred surfactants for use with the topical form of the present invention are PEG-660 15-hydroxystearate (Solutol®), PEG-15 monooleate, PEG-23 monostearate or PEG-23 monomyristate, because of their acceptable taste and odor, and the most preferred water-immiscible solvents are peppermint oil, spearmint oil, sweet orange oil and other essential oils, or ethyl oleate, propylene glycol dicaprylate, isopropyl myristate, where again the fragrance and biocompatibility play important roles in solvent selection. Some topical use examples are given in the "Examples" section below. Topical applications may be used on the skin directly, without pre-mixture with water. As such, the applications are non-greasy lotions or creams, yet because of their emulsion-forming properties, they form protective layers on skin that are easily washed away later by water alone. This feature leads to skin care products that are perfectly suitable for maintaining the skin during the nighttime, because the remaining non-ionic surfactant and all "greaseless" residues are easily removed in the morning by simply washing with water. The feature of the ability of the emulsion base product to bring hydrophobic CoQ10 to skin cells during night-time, then being easily removed with water from the skin in water-washing, makes the product perfectly matched for cosmetic use. The inventors note that Solutol-based topical products must be prepared with melted Solutol® at about 45° C., but thereafter may be stored and used at room or body temperature, as lotion or cream-like formulations.

In addition to using the present invention to prepare CoQ10 supplements that are administered orally or topically, the invention can be used to produce therapeutic agents that are delivered parenterally, as an intravenous or an intramuscular liquid injection, or delivered ophthalmically as eye drops. In intravenous and topical ophthalmic applications, the therapeutic liquid is generally prepared by dispersing an amount of the preferred base composition of the present invention into another carrier liquid, such as isotonic (0.9%) saline, or 5% dextrose (for intramuscular applications) with water, or the like. For intramuscular injection, the base is warmed to body temperature and is then injected directly into the muscle, where the base forms a microemulsion in the body's extracellular fluid, which fluid carries the CoQ10 into the lymphatic system, and thence into the body.

The preferred PEG-containing surfactants for use with the parenteral and ophthalmic forms of the present invention are Solutol® and Cremophor®, due to their acceptable biocompatibility and historical use as parenteral solubilizers. Cremaphor® is preferred for intramuscular use; while Solutol®, which is liquid at higher temperatures and, thus, must be premixed with warm water before injection, is preferred for intravenous use and as an eye drop. Further, although Cremaphor® and Solutol® are preferred, any of the previously disclosed surfactants that can be used to prepare the base composition for the capsule formulation are acceptable for use in the preparation of the parenteral or ophthalmic formulation. For parenteral or ophthalmic use, the preferred solvent is ethyl oleate, which is approved for parenteral applications as an N.F. (National Formulary) substance. In addition to ethyl oleate, with the exception of the plant essential oils, any of the previously disclosed solvents that can be used to prepare the base composition for the capsule formulation are acceptable for use in the preparation of the parenteral or ophthalmic formulation. For most parenteral and ophthalmic applications, a base composition containing a CoQ10 concentration of about 2% is possible to achieve with good stability. The base can be diluted with 3 parts of 0.9% warm saline in order to form a 0.5% CoQ10 aqueous clear microemulsion for intravenous injection or topical ophthalmic administration.

The parenteral and ophthalmic formulations are provided by using the preferred base composition of the present invention and the formulation is prepared by using the same preferred method that is used to prepare the base composition for use with a dissolvable capsule, or by using either of the two alternative methods for preparing the base for use with a dissolvable capsule. In one embodiment of a parenteral or ophthalmic formulation, CoQ10 is included in the base in an amount of about 2.0% by weight of the base, Solutol® as the PEG-containing surfactant is included in the base in an amount of about 82% by weight of the base, and ethyl oleate as the water-immiscible solvent is included in the base in an amount of about 16% by weight of the base. For intravenous and ophthalmic applications, one (1) part of the CoQ10 base composition is mixed with about three (3) to about four (4) parts of a carrier liquid, such as physiologic saline or 5% dextrose with water, which liquid has been warmed to a temperature of between about 40° C. and about 45° C. A predetermined amount of the resulting microemulsion, which contains a CoQ10 concentration of about 0.5% by weight of the microemulsion, is then suitable for intravenous or ophthalmic administration after the temperature of the microemulsion has cooled to between body temperature and room temperature, between about 37° C. and about 23° C. For intramuscular applications, the CoQ10 base composition is warmed to body temperature, between about 37° C. and about 40° C., and can then be injected directly into the muscle, where the base forms a microemulsion in the body's extracellular fluid.

The present invention discloses the use of PEG-containing surfactants and water-immiscible solvents in the preparation of a preferred base composition containing CoQ10 concentrations of up to about 20% by weight of the composition for orally administered supplements and COQ10 concentrations of up to about 2.5% for parenterally administered agents. The inventors have further determined, however, that acceptable state-of-the-art concentrations of CoQ10, of up to about 3% by weight of the base, can be prepared by using the PEG-containing surfactants without using any solvent, i.e. without using a separate hydrophobic liquid which has the purpose of solubilizing CoQ10. The use of a water-immiscible solvent is only necessary if higher concentrations of CoQ10 are desired. Accordingly, the present invention includes a solvent-free microemulsifyable base composition consisting essentially of: CoQ10 included in the composition in an amount of about 2% to about 3% by weight of the composition; and a liquid or molten PEG-containing surfactant, included in the composition in an amount of about 97% to about 98% by weight of the composition.

Preferably, for a capsule formulation, the solvent-free base composition is formed by adding a predetermined amount of the CoQ10 to a predetermined amount of the liquid or molten surfactant, preferably Cremophor® or Solutol®, and then stirring the CoQ10 and surfactant sufficiently in order to dissolve the CoQ10 into the surfactant; depending on the surfactant being used, this process can take only a few minutes to several hours to complete. The solvent-free base composition, just as in the preferred base containing a solvent, is anhydrous, homogenous, thermodynamically stable as a solution, and appears as a transparent orange-colored liquid, a characteristic of CoQ10 solutions. The solvent-free base composition can then be used to produce a capsule formulation by adding a unit dosage of the solvent-free base to a dissolvable capsule, and the solvent-free base forms a microemulsion in the same manner as the preferred base composition, when the base comes into contact with the watery gastric juices.

The solvent-free base composition can also be used in the preparation of a consumable beverage or mouthwash. The beverage can be produced by mixing about one (1) part of the solvent-free base with about two (2) parts of water in order to dilute the base composition, said water having a temperature of about 40° C. to about 50° C. Then, the diluted solvent-free base is stirred for several minutes in order to form the microemulsion, and a predetermined amount of the microemulsion can be added to a consumable beverage. For the mouthwash, however, the solvent-free base in its undiluted form can be added directly to a water-based mouthwash, and after sufficient stirring the microemulsion forms in the mouthwash. The preferred surfactants for either the beverage or the mouthwash are PEG-660 15-hydroxystearate (BASF Corporation's Solutol®), PEG-15 monooleate, PEG-23 monostearate or PEG-23 monomyristate, because of their acceptable taste and odor.

Similarly, the solvent-free base composition can be used in the preparation of parenterally and ophthalmically administered agents. For these agents, the preferred surfactants are Cremaphor® or Solutol®. If the surfactant that is included in the solvent-free base is Cremaphor®, then the microemulsion is prepared by mixing about one (1) part of the solvent-free base with about three (3) to about four (4) parts of a carrier liquid, and the microemulsion can then be used as an intravenous agent or in as an eye drop formulation. On the other hand, if the surfactant is Solutol®, then the microemulsion is prepared by mixing about one (1) part of the solvent-free base with about five (5) parts of carrier liquid. Further, the undiluted solvent-free base composition can be injected directly as an intramuscularly administered agent. The undiluted solvent-free base can also be used directly as a topically applied formulation in a lotion, cream or salve. For the topically applied formulation, the preferred surfactants are PEG-660

15-hydroxystearate (Solutol®), PEG-15 monooleate, PEG-23 monostearate or PEG-23 monomyristate, because of their acceptable taste and odor.

In addition to the preferred surfactants described above, any of the PEG-containing surfactants that are suitable for use in the capsule formulation in which a solvent is included in the base can also be used in the preparation of the solvent-free base composition.

Some comments regarding the demonstrated ability of the solvent-free base composition to form a CoQ10 microemulsion seem to be appropriate. In this regard, however, the inventors submit that the usefulness of the solvent-free base composition is not dependent upon the accuracy of any theory as to why the solvent-free base is able to form a CoQ10 microemulsion. In general, the inventors believe the ease of formation of CoQ10 microemulsions without solvent, at least for concentrations of CoQ10 of up to about 3% of the base, is explained by the basic observation that micellar microemulsion formation is not dependent on the presence of any material other than water and the appropriate surfactant itself. Thus, solvent-free micellar-type microemulsions of low concentrations of CoQ10 may be possible because microemulsions of PEG-containing surfactants containing no other elements may, in fact, be possible. In water, the micellar solutions automatically formed by the preferred class of PEG-containing surfactants do not require the presence of an interior lipid drop made of a guest hydrophobe. Rather, the hydrophobic portions of the micelle surfactants serve this purpose, as shown by the size of the smallest micelles, which have a radius of about the length of a typical surfactant molecule (about 7 nm). Light scattering studies of micellar solutions of the PEG-containing surfactants preferred in this invention, show that these micelles, and micellar solutions, form in water at very low concentrations, even when the surfactant is mixed into water alone. For example, the "critical micellar concentration" of Solutol® HS-15 in pure water is given by the manufacturer (BASF) as "0.005 and 0.002%". These concentrations are near instrument detection limits, and are small enough to lead to the assumption that a water solution of any arbitrarily small amount of pure Solutol® HS-15 contains micelles. These micelles, when carrying hydrophobic guest molecules, are microemulsions. The cores of these micelles, when not containing hydrophobic guests, are probably not hollow, but simply (as suggested by their size of about 12 nm) contain the 2 nm hydrophobic tails of the 7 nm long surfactant molecules; thus a 12 nm micelle may be expected to have a core as small as 4 nm in diameter.

The solvent-containing microemulsions of the present invention do not contain enough solvent to cause the solvent to be present as a drop in the center of a standard two-phase emulsion-a drop in which CoQ10 molecules could freely more. Rather, in micellar microemulsions, the coated CoQ10 molecules appear to be closely packed into the core of a 12 to 25 nm diameter micelle, which has a lipophilic core as small as 6 nm in diameter: the approximate length of a single CoQ10 molecule. As a result, in the emulsification process, the role of the solvent appears to be mainly to prevent CoQ10 from crystallizing out of the base, before CoQ10 can become locked into the relatively small microemulsion core, as the microemulsion forms. However, in the case of lower concentrations of CoQ10 dissolved in the surfactant without solvent, microemulsion micelles may form with the addition of water, in which CoQ10 molecules are locked into the lipophilic core of micelles without any solvent coating. The basic water-stability of surfactant micelles made out of surfactant alone is the reason why such micelles may be employed to "solubilize" and carry guest hydrophobe molecules like CoQ10, whether with or without associated "solvents."

It follows that the purpose of the solvent in the present invention is not to form a core of an emulsion drop, because no such core may exist in a small micellar microemulsion. Rather, the inventors hypothesize that the solvent in the present invention functions to individually coat the highly lipophilic and self-interactive molecules of CoQ10, so as to reduce their interaction with each other. This is suggested by the fact that the highest molar ratio of solvent to CoQ10 in the preferred embodiments is about 7:1, which is close to the needed ratio for solvent molecules to coat the exterior surface of a CoQ10 molecule, which is a little more than twice as long as the typical solvent molecule. The long and linear pi-bond rich tails of CoQ10 molecules easily form crystals, but these are prevented from forming by small-molecule lipophilic solvents which interact hydrophobically with CoQ10, but are themselves non-linear molecules containing bends or kinks, such as ketone groups and double bonds of the type that prevents these molecules from stacking well in crystals.

For all of the embodiments of the present invention, except for the topical embodiment, it is preferred that CoQ10 be used in an oxidized form (ubiquinone); alternatively, CoQ10 can be used in a reduced form (ubiquinol). For the topical embodiments, however, it is preferred that CoQ10 be used in a reduced form. If a reduced form of CoQ10 is used, then an antioxidant such as butylated hydroxytoluene (BHT) or unesterified vitamin E (d-alpha tocopherol, or other tocopherol vitomers) must be added to the base composition when it is anticipated that the CoQ10-containing supplement will come into contact with air for prolonged periods of time (weeks or more). The antioxidant should be added to the base in amounts of about one part per thousand, in order to prevent air oxidation of the reduced form into the oxidized form. Notably, gelatin liquid-filled capsules are usually relatively impermeable to oxygen, so the requirement for an antioxidant in the use of ubiquinol may be mitigated in this use.

Finally, it is a feature of the present invention that both the preferred base composition and the solvent-free base composition are easily sterilized by passing the respective base, either in its undiluted form (i.e. before it forms a microemulsion) or in its diluted form (i.e. after it forms a microemulsion), through a 0.2 micron filter.

The following examples further describe and illustrate the present invention:

EXAMPLE NO. 1

This example is chosen in order to further disclose the method of the present invention is capable of producing a base composition containing a 20% concentration of CoQ10 by weight of the base, and that the base is stable at 37° C. and is suitable for use in a unit-dosage gelatin capsule. First, 400 mg of crystalline CoQ10 is dissolved into 400 mg of 37–40° C. warm orange oil to form a 50% CoQ10 solution; this solution is then mixed with 1200 mg 37–40° C. warm cremophor under sufficient stirring to mix them completely. The warm liquid base composition is noted to have a transparent orange appearance. A unit-dosage of the base is loaded into clear gelatin capsules while it is still warm.

The filled CoQ10 capsules are now allowed to cool under reduced temperature (such as a commercial freezer) overnight to allow an excess amount of CoQ10 to re-crystallize from the solution. Returning them to room temperature for a few hours insures that the liquid is no longer supersaturated with CoQ10.

The microemulsification test is carried out as follows: 125 ml of distilled water at a temperature of 37±1° C. water is put into a 150 ml Erlenmeyer flask with a magnetic stir bar, and one capsule of the CoQ10 capsule is put into the warm water with sufficient stirring for good agitation. After stirring for 10 minutes, the gelatin capsule and its content is seen to be completely dissolved into a transparent yellow liquid mixture which appears to be a true chemical "solution." However, in a dark room, such a "solution" may be proven to be a microemulsion by shining a 5 mW 630~670 nm red diode laser beam through it. The appearance of high-angle Rayleigh-Tyndall back-scattering of laser light along the beam line, similar to that seen in Cremaphor-35® micellar solutions, demonstrates that a micelle-aggregate-sized microemulsion has formed. Therefore, the orange oil/CoQ10 composition is shown not to be "dissolved" in water but rather "microemulsified" in warm water by the surfactant.

EXAMPLE NO. 2

A base containing a 10% concentration of CoQ10 in a capsule. This example illustrates use of the solvent ethyl oleate and the surfactant Cremaphor® in combination for use in a unit dose gelatin capsule. First, 1.0 g of CoQ10 is dissolved in 3.0 g of 37~40° C. ethyl oleate to form a 25% CoQ10 solution; this solution is then mixed with 6.0 g 37~40° C. warm cremophor under sufficient stirring to mix them completely. The warm liquid contains 10% CoQ10 by weight of the base. It is noted to have a transparent orange appearance. A unit-dosage of the base is loaded into clear gelatin capsules while it is still warm. After a time at room temperature, it may show CoQ10 re-crystallization, but under body temperature (37° C.), these crystals will dissolve in solution in a few minutes, allowing this mixture to be used as a filler for a soft gelatin, which still gives good microemulsions on stirring with body temperature water.

After being put in a commercial freezer for several hours to ensure crystallization, then allowed to warm to room temperature (23° C.) for several hours, all capsules will show crystallization, but most of the $CoQ_{10}$ re-dissolves into the liquid. After the capsule makes contact with 37° C. water, the remaining crystals will first melt, then disperse as clear microemulsion.

EXAMPLE NO. 3

An example of a high concentration (15%), CoQ10-containing capsule. CoQ10 microemulsion base using Cremaphor®-35, which is stable at room temperature (23° C.) and suitable for unit dose gelatin capsule use, where a clear liquid gel capsule is desired. First, 1.5 g of CoQ10 is first dissolved into 2.25 grams orange oil at 27° C., then 6.25 grams of Cremaphor®-35 is added, stirring until completely mixed. The warm liquid is noted to have a transparent orange appearance. It may be cooled to room temperature without re-crystallization, and if re-crystallization occurs at lower temperatures (i.e., below 25° C.), it will reverse at room temperature. This composition is suitable for making microemulsions of CoQ10 at room temperature (23° C.) or above.

After being put in a commercial freezer for several hours to ensure crystallization, then allowed to warm to room temperature (23° C.) for several hours, most of the CoQ10 will re-dissolve in the base liquid. After the capsule makes contact with 37° C. water, the remaining crystals will first melt, then disperse as clear microemulsion when the base makes contact with warm water.

EXAMPLE NO. 4

An example of high concentration (15%) CoQ10 microemulsion base which is stable to re-crystallization at high room temperature (25° C. to 27° C.), and is suitable for use in beverages. First, 1.5 g of CoQ10 is dissolved into 2.5 grams, 40° C. orange oil; then 6.0 grams of molten Solutol® liquid is added, stirring until all solid particles are dissolved. The warm liquid base composition is noted to have a transparent orange appearance. It may be cooled to room temperature without re-crystallization, or it may be cooled to lower temperatures (causing appearance of a CoQ10 microcrystal suspension) and then returned to 27° C., with disappearance of all suspended CoQ10 precipitate. This base will emulsify in water solutions at 27° C. or higher temperatures. It is suitable for addition to fluid beverages, where it imparts a pleasant orange fragrance. Solutol-based liquid base formulas may show phase separation of liquids on standing, possibly due to the PEG component of Solutol®, but these may be remixed before addition of water, without hampering the microemulsion process.

EXAMPLE NO. 5

Preparation of a 12% CoQ10 formulation, which is stable at room temperature (23° C.) and is suitable for clear capsule preparations, or for topical preparations. First, 1.2 g of CoQ10 is dissolved into 2.0 grams of orange oil at 40° C.; then 6.8 grams of molten Solutol® liquid is added, stirring until all CoQ10 particles are dissolved. The warm liquid is noted to have a transparent orange appearance. Again, Solutol-based liquid base formulas may show phase separation of liquids on standing, possibly due to the known inactive unesterified PEG component of Solutol®, but these may be remixed before or during the addition of water, without harming the microemulsion process.

EXAMPLE NO. 6

An example of the use of the solvent ethyl oleate and the surfactant Cremaphor® for a 2.5% CoQ10 product which is stable at room temperature, and suitable for parenteral use. First, 110 mg of CoQ10 is first dissolved into 890 mg of 37~40° C. warm ethyl oleate to form an 11% CoQ10 solution; this solution is then mixed with 3.4 grams of 37~40° C. warm Cremophor® under sufficient stirring to mix them completely. The warm liquid is noted to have a transparent orange appearance. After warming to body temperature it may be injected directly intramuscularly in mammals, or it may be mixed into physiological saline at a ratio of 1 part base to 4 parts saline, for a parenteral microemulsion which is 0.5% CoQ10 by weight, and which is suitable for intravenous administration.

When the above base is used in a unit dose capsule, it may be tested by being put in a commercial freezer for several hours to ensure crystallization, then allowed to warm to room temperature (23° C.) for several hours. It will be seen that most of the CoQ10 re-dissolves as a semi-liquid. After the capsule makes contact with 37° C. water, the remaining crystals will first melt, then disperse as clear microemulsion.

EXAMPLE NO. 7

An example of the use of the solvent ethyl oleate and the surfactant Solutol® for a 2% CoQ10 product which is stable at room temperature, and suitable for topical or intravenous parenteral use. First, 110 mg of CoQ10 is dissolved into 890 mg of 37~40° C. warm ethyl oleate to form an 11% CoQ10 solution; this solution is then mixed with 4.5 grams of Solutol® warmed to 45° C. and stirred sufficiently to mix them completely. The warm liquid is noted to have a transparent orange appearance. It may be cooled to room temperature (23° C.) and remains liquid, in which form it may be used as a 2% topical CoQ10 treatment formula. For IV parenteral use, it may be mixed at 40° C. into physiological saline at a ratio of 1 part base to 3 parts saline, for a parenteral microemulsion which is stable at body temperature (37° C.), and which is 0.5% CoQ10 by weight, and which is suitable for intravenous administration.

If the above composition is put into a commercial freezer for several hours to ensure CoQ10 crystallization, then allowed to warm to room temperature (23° C. to 25° C.) for several hours, most of the CoQ10 re-dissolves as a semi-liquid. After the capsule makes contact with 37° C. water, the remaining crystals will first melt, then disperse as clear microemulsion.

EXAMPLE NO. 8

An example of the use of only the surfactant Cremaphor®-35 with no solvent, to prepare a 2% CoQ10 product which is stable at room temperature, and suitable for I.M. or I.V. parenteral use. First, 100 mg of CoQ10 is dissolved into 4900 mg of 40~45° C. warm Cremaphor® with sufficient stirring to form 2% CoQ10 solution. This requires 5 to 10 minutes. The warm liquid is noted to have a transparent orange appearance. After CoQ10 crystals are dissolved, the mixture may be cooled to room temperature, at which it remains a transparent orange liquid. For I.V. (intravenous) parenteral use, it may be again melted at 40-45° C. and mixed into physiological saline at 40-45° C. in a ratio of 1 part base to 3 parts water, for a parenteral microemulsion which is stable at body temperature, and which is 0.5% CoQ10 by weight, and which is suitable for intravenous administration. For I.M. (intramuscular) parenteral use, it may be injected directly into the muscle, as the (anhydrous) 2% CoQ10 emulsion base.

EXAMPLE NO. 9

An example of the use of only the surfactant Solutol® with no solvent, to prepare a 3% CoQ10 product which is stable at room temperature, and suitable for topical or intravenous parenteral use. First, 150 mg of CoQ10 is dissolved into 4850 mg of 40~45° C. warm Solutol® with sufficient stirring to form 3% CoQ10 solution. This requires 5 to 10 minutes. The warm liquid is noted to have a transparent orange appearance. It should be noted that the minimal solution temperature required with no use of solvent, as in this example and the one below, is several degrees OC higher than needed for examples in which solvent is used. After CoQ10 crystals are dissolved, the mixture may be cooled to room temperature, at which it becomes a pasty orange lotion, creamy solid. For IV parenteral use, it may be again melted at 40-45° C. and mixed into physiological saline at 40-45° C. in a ratio of 1 part base to 5 parts water, for a parenteral microemulsion which is stable at body temperature, and which is 0.5% CoQ10 by weight, and which is suitable for intravenous administration.

Although the present invention has been described in its preferred embodiment and in certain other embodiments, it will be recognized by those skilled in the art that other embodiments and features may be provided without departing from the scope of the invention, which is defined by the appended claims.

We claim:

1. A self-microemulsifiable anhydrous base composition, comprising:
   a) CoQ10 in an effective amount of about 12% to about 20% by weight of the composition;
   b) a water-immiscible solvent in the form of a plant essential oil in an effective amount of up to about 30% by weight of the composition; and
   c) a nonionic surfactant in an effective amount of about 60% to about 82% by weight of the composition, with the nonionic surfactant selected from the group consisting of:
      i) a first non-ionic surfactant having the structure of [POE(n)]subm-R'-R; where POE is a polyoxyethylene moiety of -mer number n, and having m of these POE functional groups attached to R'; where the value of m is one to three; where R' is a linking moiety selected from glyceryl, sorbitan, ester, amino, or ether functions; where R is a hydrophobic moiety consisting of saturated or unsaturated alkyl or alkylphenyl groups; and where the structure of the first non-ionic surfactant is further defined by a ratio of A, the total number of POE -mer units in the surfactant given by the product of -mer number n and total PEG chain number m per molecule, to B, the number of carbons in the hydrophobic functional group R, with the ratio of A/B being in the range of about 1 to 2 or in the range of about 0.7 to 4; and
      ii) a second nonionic surfactant having the structure of [R'-(POE) subn]sub3-glyceride, where POE is a polyoxyethylene moiety of -mer number n, inserted between fatty acid acyl residues R' and a glycerol residue, which had been attached, before polyethoxylation, directly to the acyl residues as a common triglyceride, and where structure of the second non-ionic surfactant is further defined by a ratio of A, the total number of POE -mer units in the surfactant given by the product of -mer number n and total PEG chain number 3 per molecule, to B, the number of carbons in the 3 fatty acid R' residues, with the ratio of A/B being in the range of about 0.5 to 3 or in the range from about 0.6 to 1.5.

2. The base composition as in claim 1 in which the plant essential oil is a terpenoid-based plant essential oil, containing as a primary ingredient a monoterpene.

3. The base composition as in claim 2 in which the monoterpene is limonene or myrcene.

4. The base composition as in claim 1 in which the plant essential oil is a terpenoid-based plant essential oil, containing as a primary ingredient a sesquiterpene.

5. The base composition as in claim 4 in which the sesquiterpene is cedrene or farnescene.

6. The base composition as in claim 1 in which the plant essential oil is a terpenoid ketone-based plant essential oil.

7. The base composition as in claim 6 in which the terpenoid ketone-based plant essential oil is a carvone based essential oil.

8. The base composition as in claim 7 in which the carvone based essential oil is spearmint oil or kuromoji oil.

9. The base composition as in claim 1 in which the plant essential oil is a fenchone-based oil.

10. The base composition as in claim 9 in which the fenchone-based oil is fennel oil.

11. The base composition as in claim 1 in which the plant essential oil is a camphor-based oil.

12. The base composition as in claim 11 in which the camphor-based oil is rosemary oil.

13. The base composition as in claim 1 in which the plant essential oil contains a terpenoid alcohol.

14. The base composition as in claim 13 in which the terpenoid alcohol is linalool, geraniol, citronelloi, or farnesol.

15. The base composition as in claim 1 in which the plant essential oil contains a derivative of terpenoid alcohol.

16. The base composition as in claim 15 in which the derivative of terpenoid alcohol is acetate, butyrate, benzolate or anthranylate.

17. The base composition as in claim 1 in which the plant essential oil contains a terpenoid aldehyde.

18. The base composition as in claim 17 in which the terpenoid aldehyde is citral, citronellal, or geranial.

19. The base composition as in claim 1 in which the plant essential oil is a citrus-derived oil.

20. The base composition as in claim 19 in which the citrus-based oil is sweet orange oil, bitter orange oil, eau de brouts oil, petitgrain oil, neroli oil, lime oil, grapefruit oil, lemon oil, tangerine oil, mandarin oil, or tangelo oil.

21. The base composition as in claim 1 in which the plant essential oil is selected from the group consisting of Abies Alba, ale (various pine species), ambrette seed, angelica seed, benzoin (*Styrax benzoin*), bergamot (*C. bergamia*), bergamot mint (*M. citrata*), cabreuva, cananga, carrot seed, cascarilla, Atlas cedarwood (*C. atlantica*), Texas cedarwood (*J. mexicana*), Virginian cedarwood (*J. virginiana*), celery seed, German camomile (*C. recutita*), Roman Camomile (*A. nobilis*), citronella (*C. nardus*), French clary sage (*S. sclarea*), copaiba, cuceb, cypress, davana, deertongue, fenugreek, Canadian fir needle (*A. balsamea*), galbanum, geranium (*P. graviolens*), ginger, gurjun, hay, hibawood, immortelle, jasmine, juniperberry, labdanum, lavandin, lavender, lemongrass (*C. citratus* or *C. flexosis*), linaloe, Spanish marjoram (*T. masticina*), may chang, mimosa, myrtle, palmarosa, patchouli, black pepper, Peru balsam, Peruvian pepper (*S. molle*), Phoenecian juniper (*J. phoenicea*), Scotch pine (*P. sylvestris*), Bulgarian or Moroccan rose (*R. damascena*), rosemary, Spanish sage (*S. lavandulaefolia*), snakeroot, spearmint, hemlock spruce oil (*T. canadensis*), turmeric, and ylang-ylang.

22. The base composition as in claim 1 in which the plant essential oil is an absolute plant oil.

23. The base composition as in claim 22 in which the absolute plant oil is selected from the group consisting of broom oil (*S. junceum*), mastic oil (*P. lentiscus*) verbena oil (*L. citriodora*), narcissus oil, orange flower oil, cabbage rose oil (*R. centifolia*), and tobacco leaf oil (*N. affinis*).

24. The base composition as in claim 1 in which the water-immiscible solvent is a purified biocompatible chemical extracted from a plant essential oil.

25. The base composition as in claim 24 in which the purified biocompatible chemical is selected from the group consisting of d-limonene, l-limonene, d-carvone, l-carvone, l-linalyl acetate, l-linalool, geranyl acetate, farnesol, and farnesyl acetate.

26. The base composition of claim 1 in which the first nonionic surfactant is selected from the group consisting of PEG-15 monolaurate, PEG-20 monolaurate, PEG-32 monolaurate, PEG-48 monolaurate, PEG-13 monoleate, PEG-15 monooleate, PEG-20 monooleate, PEG-32 monooleate, PEG-72 monoleate, PEG-15 monostearate, PEG-660 15-hydroxystearate, PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate, PEG-20 sorbitan monolaurate, PEG-20 sorbitan monopalmitate, and PEG 20 sorbitan stearate, PEG-40 sorbitan monooleate, PEG-80 sorbitan monolaurate, POE-23 lauryl ether, POE-20 oleyl ether, PEG 30-60 nonyl phenol series, PEG 30-55 octyl phenol series, and mixtures thereof.

27. The base composition of claim 1 in which the second nonionic surfactant is selected from the group consisting of PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, and PEG-60 corn oil, and mixtures thereof.

28. The base composition of claim 1 in which the nonionic surfactant is Solutol® HS-15.

29. The base composition of claim 1 in which the nonionic surfactant is Cremaphor®-35.

30. A self-microemulsifiable anhydrous base composition, comprising:
   a) a CoQ substance in an effective amount of about 12% to about 20% by weight of the composition;
   b) a water-immiscible solvent in the form of a plant essential oil in an effective amount of up to about 30% by weight of the composition; and
   c) a nonionic surfactant in an effective amount of about 60% to about 82% by weight of the composition, with the nonionic surfactant selected from the group consisting of:
      i) a first non-ionic surfactant having the structure of [POE(n)]subm-R'-R; where POE is a polyoxyethylene moiety of -mer number n, and having m of these POE functional groups attached to R'; where the value of m is one to three; where R' is a linking moiety selected from glyceryl, sorbitan, ester, amino, or ether functions; where R is a hydrophobic moiety consisting of saturated or unsaturated alkyl or alkylphenyl groups; and where the structure of the first non-ionic surfactant is further defined by a ratio of A, the total number of POE -mer units in the surfactant given by the product of -mer number n and total PEG chain number m per molecule, to B, the number of carbons in the hydrophobic functional group R, with the ratio of A/B being in the range of about 1 to 2 or in the range of about 0.7 to 4; and
      ii) a second nonionic surfactant having the structure of [R'-(POE) subn]sub3-glyceride, where POE is a polyoxyethylene moiety of -mer number n, inserted between fatty acid acyl residues R' and a glycerol residue, which had been attached, before polyethoxylation, directly to the acyl residues as a common triglyceride, and where structure of the second non-ionic surfactant is further defined by a ratio of A, the total number of POE -mer units in the surfactant given by the product of -mer number n and total PEG chain number 3 per molecule, to B, the number of carbons in the 3 fatty acid R' residues, with the ratio of A/B being in the range of about 0.5 to 3 or in the range from about 0.6 to 1.5.

31. The base composition of claim 30 in which the CoQ substance is selected from the group consisting of CoQ1, CoQ2, CoQ3, CoQ4, CoQ5, CoQ6, CoQ7, CoQ8 and CoQ9.

32. The base composition of claim 1 or claim 30 in which the base composition is contained within a dissolvable capsule.

33. The base composition of claim 1 or 30 in which the base composition comprises a carrier liquid.

34. The base composition of claim 1 or 30 in which the base composition comprises a beverage or mouthwash.

35. A self-microemulsifiable anhydrous base composition, comprising:
  a) CoQ10 in an effective amount of about 2% to about 10% 20% by weight of the composition;
  b) a water-immiscible solvent in the form of a monoester derived from an aliphatic acid and a monoalcohol in an effective amount of up to about 30% by weight of the composition; and
  c) a nonionic surfactant in an effective amount of about 60% to about 82% by weight of the composition, with the nonionic surfactant selected from the group consisting of:
    i) a first non-ionic surfactant having the structure of [POE(n)]subm-R'-R; where POE is a polyoxyethylene moiety of -mer number n, and having m of these POE functional groups attached to R'; where the value of m is one to three; where R' is a linking moiety selected from glyceryl, sorbitan, ester, amino, or ether functions; where R is a hydrophobic moiety consisting of saturated or unsaturated alkyl or alkylphenyl groups; and where the structure of the first non-ionic surfactant is further defined by a ratio of A, the total number of POE -mer units in the surfactant given by the product of -mer number n and total PEG chain number m per molecule, to B, the number of carbons in the hydrophobic functional group R, with the ratio of NB being in the range of about 1 to 2 or in the range of about 0.7 to 4; and
    ii) a second nonionic surfactant having the structure of [R'-(POE) subn]sub3-glyceride, where POE is a polyoxyethylene moiety of -mer number n, inserted between fatty acid acyl residues R' and a glycerol residue, which had been attached, before polyethoxylation, directly to the acyl residues as a common triglyceride, and where structure of the second non-ionic surfactant is further defined by a ratio of A, the total number of POE -mer units in the surfactant given by the product of -mer number n and total PEG chain number 3 per molecule, to B, the number of carbons in the 3 fatty acid R' residues, with the ratio of A/B being in the range of about 0.5 to 3 or in the range from about 0.6 to 1.5.

36. The base composition as in claim 35 in which the monoester is selected from the group consisting of ethyl oleate, isopropyl myristate, ethyl laurate, butyl oleate, oleyl acetate, oleyl propionate, octyl octanoate, octyl decanonate, and oleyl oleate.

37. The base composition of claim 35 in which the first nonionic surfactant is selected from the group consisting of PEG-15 monolaurate, PEG-20 monolaurate, PEG-32 monolaurate, PEG-48 monolaurate, PEG-13 monooleate, PEG-15 monooleate, PEG-20 monooleate, PEG-32 monooleate, PEG-72 monooleate, PEG-15 monostearate, PEG-660 15-hydroxystearate, PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate, PEG-20 sorbitan monolaurate, PEG-20 sorbitan monopalmitate, and PEG 20 sorbitan stearate, PEG-40 sorbitan monooleate, PEG-80 sorbitan monolaurate, POE-23 lauryl ether, POE-20 oleyl ether, PEG 30-60 nonyl phenol series, PEG 30-55 octyl phenol series, and mixtures thereof.

38. The base composition of claim 35 in which the second nonionic surfactant is selected from the group consisting of PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, and PEG-60 corn oil, and mixtures thereof.

39. The base composition of claim 35 in which the nonionic surfactant is Solutol® HS-15.

40. The base composition of claim 35 in which the nonionic surfactant is Cremaphor®-35.

41. A self-microemulsifiable anhydrous base composition, comprising:
  a) CoQ10 in an effective amount of about 2% to about 3% by weight of the composition; and
  b) a non-ionic surfactant in an effective amount of about 97% to about 98% by weight of the composition, with the nonionic surfactant selected from the group consisting of:
    i) a first non-ionic surfactant having the structure of [POE(n)]subm-R'-R; where POE is a polyoxyethylene moiety of -mer number n, and having m of these POE functional groups attached to R'; where the value of m is one to three; where R' is a linking moiety selected from glyceryl, sorbitan, ester, amino, or ether functions; where R is a hydrophobic moiety consisting of saturated or unsaturated alkyl or alkylphenyl groups; and where the structure of the first non-ionic surfactant is further defined by a ratio of A, the total number of POE -mer units in the surfactant given by the product of -mer number n and total PEG chain number m per molecule, to B, the number of carbons in the hydrophobic functional group R, with the ratio of A/B being in the range of about 1 to 2 or in the range of about 0.7 to 4; and
    ii) a second nonionic surfactant having the structure of [R'-(POE) subn]sub3-glyceride, where POE is a polyoxyethylene moiety of -mer number n, inserted between fatty acid acyl residues R' and a glycerol residue, which had been attached, before polyethoxylation, directly to the acyl residues as a common triglyceride, and where structure of the second non-ionic surfactant is further defined by a ratio of A, the total number of POE -mer units in the surfactant given by the product of -mer number n and total PEG chain number 3 per molecule, to B, the number of carbons in the 3 fatty acid R' residues, with the ratio of A/B being in the range of about 0.5 to 3 or in the range from about 0.6 to 1.5.

42. The base composition of claim 41 in which the first nonionic surfactant is selected from the group consisting of PEG-15 monolaurate, PEG-20 monolaurate, PEG-32 monolaurate, PEG-48 monolaurate, PEG-13 monooleate, PEG-15 monooleate, PEG-20 monooleate, PEG-32 monooleate, PEG-72 monooleate, PEG-15 monostearate, PEG-660 12-hydroxystearate (Solutol HS 15), PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate, PEG-20 sorbitan monolaurate, PEG-20 sorbitan monopalmitate, and PEG 20 sorbitan stearate, PEG-40 sorbitan monooleate, PEG-80 sorbitan monolaurate, POE-23 lauryl ether, POE-20 oleyl ether, PEG 30-60 nonyl phenol series, PEG 30-55 octyl phenol series, and mixtures thereof.

43. The base composition of claim 41 in which the second nonionic surfactant is selected from the group consisting of PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, and PEG-60 corn oil, and mixtures thereof.

44. The base composition of claim 41 in which the nonionic surfactant is Solutol® HS-15.

45. The base composition of claim 41 in which the nonionic surfactant is Cremaphor®-35.

* * * * *